(12) United States Patent
Ryan (10) Patent No.: US 12,263,120 B2
(45) Date of Patent: Apr. 1, 2025

(54) INFUSION DEVICE AND METHOD (71) Applicant: Edwin Ryan, St. Paul, MN (US)

(72) Inventor: Edwin Ryan, St. Paul, MN (US)

(73) Assignee: Edwin Ryan, St. Paul, MN (US)

( * ) Notice: Subject to any disclaimer, the term of this patent is extended or adjusted under 35 U.S.C. 154(b) by 0 days.

(21) Appl. No.: 18/238,348

(22) Filed: Aug. 25, 2023

(65) Prior Publication Data
US 2023/0398022 A1 Dec. 14, 2023

Related U.S. Application Data (63) Continuation of application No. 14/885,274, filed on Oct. 16, 2015, now abandoned.

(60) Provisional application No. 62/154,462, filed on Apr. 29, 2015, provisional application No. 62/065,428, filed on Oct. 17, 2014.

(51) Int. Cl.
A61F 9/00 (2006.01)
(52) U.S. Cl.
CPC .... A61F 9/0026 (2013.01); A61F 2009/0052 (2013.01)
(58) Field of Classification Search
CPC .... A61F 9/0026; A61F 9/0008; A61F 9/0017; A61F 9/007; A61F 9/00; A61F 2009/0052; A61F 2009/0035; A61F 2009/0043; A61M 5/1414; A61M 5/1415; A61M 5/1417; A61M 5/1418; A61M 2005/1416; A61M 2005/1586; A61M 25/02; A61M 2025/0206; A61M 2025/0213; A61M 2025/024; A61M 2025/0246; A61M 2025/0253; A61M 2025/026; A61M 2025/0266; A61M 2025/0273; A61M 2025/028; A61M 2025/0286; A61M 2025/0293; A61M 2210/0612; A61B 50/20; A61J 15/0053; A61J 15/0057; A61J 15/0061; A61J 15/0065; Y10S 128/26; Y10S 128/06
See application file for complete search history.

(56) References Cited

U.S. PATENT DOCUMENTS 3,059,645 A  10/1962  Hasbrouck et al.
3,630,195 A  12/1971  Santomieri
(Continued)

FOREIGN PATENT DOCUMENTS

DE  2051239  5/1971
NL  2015630  4/2017
(Continued)

OTHER PUBLICATIONS

"Netherland Application Serial No. 2015630, Office Action mailed Dec. 22, 2016", 6 pgs.
(Continued)

Primary Examiner — Joel M Attey
Assistant Examiner — Alexandra Lalonde
(74) Attorney, Agent, or Firm — Schwegman Lundberg & Woessner, P.A.

(57) ABSTRACT

An ophthalmic infusion support and associated methods are shown. The ophthalmic infusion support devices include a base unit, a fixation device coupled to a bottom surface of the base unit, and an infusion tube holding device configured to hold a loop of an infusion tube at an angle projecting upward from a patient.

6 Claims, 7 Drawing Sheets

(56) References Cited

U.S. PATENT DOCUMENTS

| | | | |
|---|---|---|---|
| 3,664,340 A | | 5/1972 | Morgan |
| 3,834,380 A | * | 9/1974 | Boyd .................. A61M 25/02 128/DIG. 26 |
| 4,633,863 A | * | 1/1987 | Filips .................. A61M 25/02 128/877 |
| 4,798,599 A | | 1/1989 | Thomas |
| 5,685,841 A | | 11/1997 | Mackool |
| 5,702,371 A | | 12/1997 | Bierman |
| 2002/0092529 A1 | | 7/2002 | Rozier et al. |
| 2007/0106222 A1 | * | 5/2007 | Bennett ................. A61M 25/02 604/174 |
| 2008/0319402 A1 | | 12/2008 | Howlett et al. |
| 2009/0137962 A1 | | 5/2009 | Bracken et al. |
| 2009/0149814 A1 | | 6/2009 | Bailey et al. |
| 2009/0192458 A1 | * | 7/2009 | Wang ................... A61F 9/0017 604/117 |
| 2012/0271240 A1 | | 10/2012 | Andino et al. |
| 2016/0106579 A1 | | 4/2016 | Ryan |

FOREIGN PATENT DOCUMENTS

| | | |
|---|---|---|
| WO | 2007104350 | 9/2007 |
| WO | 2015102963 | 7/2015 |

OTHER PUBLICATIONS

"U.S. Appl. No. 14/885,274, Restriction Requirement mailed Feb. 20, 2018", 9 pgs.

"U.S. Appl. No. 14/885,274, Response filed Apr. 20, 2018 to Restriction Requirement mailed Feb. 20, 2018", 8 pgs.

"U.S. Appl. No. 14/885,274, Non Final Office Action mailed May 14, 2018", 15 pgs.

"U.S. Appl. No. 14/885,274, Respnse filed Aug. 14, 2018 to Non Final Office Action mailed May 14, 2018", 9 pgs.

"U.S. Appl. No. 14/885,274, Final Office Action mailed Nov. 23, 2018", 14 pgs.

"U.S. Appl. No. 14/885,274, Response filed Mar. 14, 2019 to Final Office Action mailed Nov. 23, 2018", 8 pgs.

"U.S. Appl. No. 14/885,274, Final Office Action mailed Apr. 11, 2019", 13 pgs.

"U.S. Appl. No. 14/885,274, Response filed Jun. 11, 2019 to Final Office Action mailed Apr. 11, 2019", 8 pgs.

"U.S. Appl. No. 14/885,274, Advisory Action mailed Jun. 25, 2019", 3 pgs.

"U.S. Appl. No. 14/885,274, Non-Final Office Action mailed Aug. 6, 2019", 20 pgs.

"U.S. Appl. No. 14/885,274, Response filed Feb. 6, 2020 to Non Final Office Action mailed Aug. 6, 2019", 8 pgs.

"U.S. Appl. No. 14/885,274, Final Office Action mailed May 4, 2020", 15 pgs.

"U.S. Appl. No. 14/885,274, Response filed Aug. 4, 2020 to Final Office Action mailed May 4, 2020", 7 pgs.

"U.S. Appl. No. 14/885,274, Advisory Action mailed Aug. 11, 2020", 3 pgs.

"U.S. Appl. No. 14/885,274, Response filed Oct. 5, 2020 to Advisory Action mailed Aug. 11, 2020", 7 pgs.

"U.S. Appl. No. 14/885,274, Non Final Office Action mailed Dec. 22, 2020", 20 pgs.

"U.S. Appl. No. 14/885,274, Response filed Apr. 22, 2021 to Non Final Office Action mailed Dec. 22, 2020", 8 pgs.

"U.S. Appl. No. 14/885,274, Final Office Action mailed May 5, 2021", 22 pgs.

"U.S. Appl. No. 14/885,274, Response filed Jul. 6, 2021 to Final Office Action mailed May 5, 2021", 8 pgs.

"U.S. Appl. No. 14/885,274, Advisory Action mailed Jul. 26, 2021", 3 pgs.

"U.S. Appl. No. 14/885,274, Non Final Office Action mailed Aug. 12, 2021", 16 pgs.

"U.S. Appl. No. 14/885,274, Response filed Nov. 12, 2021 to Non Final Office Action mailed Aug. 12, 2021", 9 pgs.

"U.S. Appl. No. 14/885,274, Final Office Action mailed Feb. 18, 2022", 22 pgs.

"U.S. Appl. No. 14/885,274, Response filed May 18, 2022 to Final Office Action mailed Feb. 18, 2022", 9 pgs.

"U.S. Appl. No. 14/885,274, Non Final Office Action mailed Jun. 6, 2022", 23 pgs.

"U.S. Appl. No. 14/885,274, Response filed Oct. 6, 2022 to Non Final Office Action mailed Jun. 6, 2022", 10 pgs.

"U.S. Appl. No. 14/885,274, Final Office Action mailed Dec. 20, 2022", 26 pgs.

"U.S. Appl. No. 14/885,274, Response filed Feb. 21, 2023 to Final Office Action mailed Dec. 20, 2022", 10 pgs.

"U.S. Appl. No. 14/885,274, Advisory Action mailed Mar. 6, 2023", 2 pgs.

"U.S. Appl. No. 14/885,274, Non Final Office Action mailed May 9, 2023", 24 pgs.

"U.S. Appl. No. 14/885,274, Response filed Aug. 9, 2023 to Non Final Office Action mailed May 9, 2023", 9 pgs.

"U.S. Appl. No. 14/885,274, Final Office Action mailed Sep. 22, 2023", 26 pgs.

U.S. Appl. No. 14/885,274, filed Oct. 16, 2015, Infusion Device and Method.

* cited by examiner

INFUSION DEVICE AND METHOD

CLAIM OF PRIORITY

This application is a continuation of and claims the benefit of priority under 35 U.S.C. § 120 to U.S. patent application Ser. No. 14/885,274, filed on Oct. 16, 2015, which claims the benefit priority to U.S. Provisional Patent Application No. 62/065,428, filed Oct. 17, 2014, and to U.S. Provisional Patent Application No. 62/154,462, filed Apr. 29, 2015 which are incorporated herein by reference in their entirety.

TECHNICAL FIELD

This invention relates to devices and methods for ophthalmological procedures, such as an infusion procedure.

BACKGROUND

A number of ophthalmological procedures require the use of an infusion line. Infusion lines have weight, and in some cases, may tend to flex as they hang from their coupling location on a patient's eye. It is desirable to avoid kinking and/or twisting of the infusion line, which may cause problems such as restricting fluid flow.

DETAILED DESCRIPTION

In the following detailed description, reference is made to the accompanying drawings which form a part hereof, and in which is shown, by way of illustration, specific embodiments in which the invention may be practiced. In the drawings, like numerals describe substantially similar components throughout the several views. These embodiments are described in sufficient detail to enable those skilled in the art to practice the invention. Other embodiments may be utilized and structural, or logical changes, etc. may be made without departing from the scope of the present invention.

Figure 1:
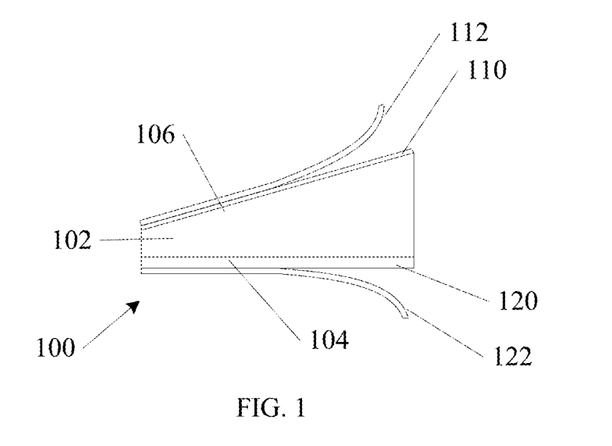
FIG. 1 shows an ophthalmic infusion support according to an embodiment of the invention.

FIG. 1 shows an ophthalmic infusion support 100 according to one example of the invention. The ophthalmic infusion support 100 includes a base unit 102 having a bottom surface 104 and a top surface 106. In one example the base unit 102 is substantially flat in one dimension (for example in the plane of the page of FIG. 1). In such an example the base unit 102 may be cut from a sheet of material, such as a closed or open cell polymer foam sheet. In one example, a resilient material such as foamed polymer sheet provides a desirable level of compliance that may allow a user to conform the ophthalmic infusion support 100 to a patient for improved fixation as discussed below. In other examples, the base unit 102 may be molded from a compliant polymer, or rigid polymer. Other materials such as metals are also possible, but may add unwanted cost to the ophthalmic infusion support 100.

In the example of FIG. 1, an adhesive 120 is coupled to the bottom surface 104. The adhesive serves as a fixation device, and may be used to attach to a patient. In one example the adhesive such as a pressure sensitive adhesive is used. In the example of FIG. 1, a peel off backing 122 is shown that may be removed to expose the adhesive 120 for attaching to a patient.

In one example, the adhesive 120 is used to attach directly to a patient, such as adhering to the patient's skin in a region adjacent to an eye, as will be discussed in more detail below. In one example, a fixation device, such as the adhesive 120 is used to attach indirectly to a patient, such as attaching to a surgical drape that is place on the patient. Both direct fixation, and indirect fixation methods are encompassed in the present disclosure. Any number of suitable adhesives may be used as a fixation device, as discussed above. Other fixation devices include, but are not limited to, mechanical fixation, such as spring clips, pins, etc. Mechanical fixation device examples will primarily be used for indirect fixation to an intermediate element, such as a surgical drape.

The ophthalmic infusion support 100 of FIG. 1 further shows an infusion tube holding device 110 coupled to the top surface 106 of the base unit 102. In the example of FIG. 1, the infusion tube holding device 110 includes an adhesive 110. The adhesive 110 may be the same or similar adhesive to the adhesive 120. In one example, a first adhesive 110 is chosen to securely hold an infusion tube, while a second, different adhesive 120 is chosen to adhere to the patient, either directly or indirectly.

In one example an adhesive such as a pressure sensitive adhesive is used for the infusion tube holding device 110. Similar to the adhesive 120, in the example of FIG. 1, a peel off backing 112 is shown that may be removed to expose the adhesive 110 for attaching to an infusion tube.

Although an adhesive is shown as the infusion tube holding device 110, the invention is not so limited. Other infusion tube holding devices may include mechanical holding devices, such as clips, clamps, fasteners, zip ties, etc. may be used as an infusion tube holding device 110.

Figure 2:
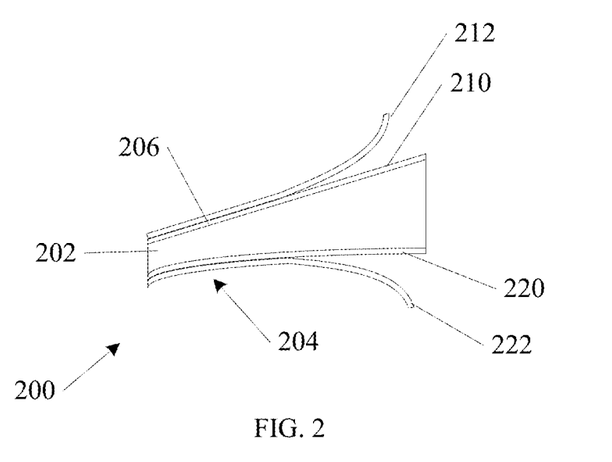
FIG. 2 shows another ophthalmic infusion support according to an embodiment of the invention.

FIG. 2 shows an ophthalmic infusion support 200 according to an example of the invention. The ophthalmic infusion support 200 includes a base unit 202 having a bottom surface 204 and a top surface 206. Similar to the ophthalmic infusion support 100, in one example the base unit 102 is substantially flat in one dimension (for example in the plane of the page of FIG. 1). As described above, materials for the base unit 202 may include, but are not limited to, polymers, foamed polymers, metals, composites, etc.

Similar to the example of FIG. 1, an adhesive 220 is coupled to the bottom surface 204. The adhesive serves as a fixation device, and may be used to attach to a patient, directly or indirectly as discussed above. In one example the adhesive such as a pressure sensitive adhesive is used. In the example of FIG. 2, a peel off backing 222 is shown that may be removed to expose the adhesive 220 for attaching to a patient. In the example of FIG. 2, the bottom surface 204 is anatomically curved to better conform and adhere to a patient, either directly or indirectly.

Similar to the example of FIG. 1, in one example an infusion tube holding device 210 is coupled to the top surface 206 of the base unit 202. In the example of FIG. 2, the infusion tube holding device 201 includes an adhesive 210. In one example an adhesive such as a pressure sensitive adhesive is used for the infusion tube holding device 210. Similar to the adhesive 220, a peel off backing 212 is shown that may be removed to expose the adhesive 210 for attaching to an infusion tube.

Figure 3:
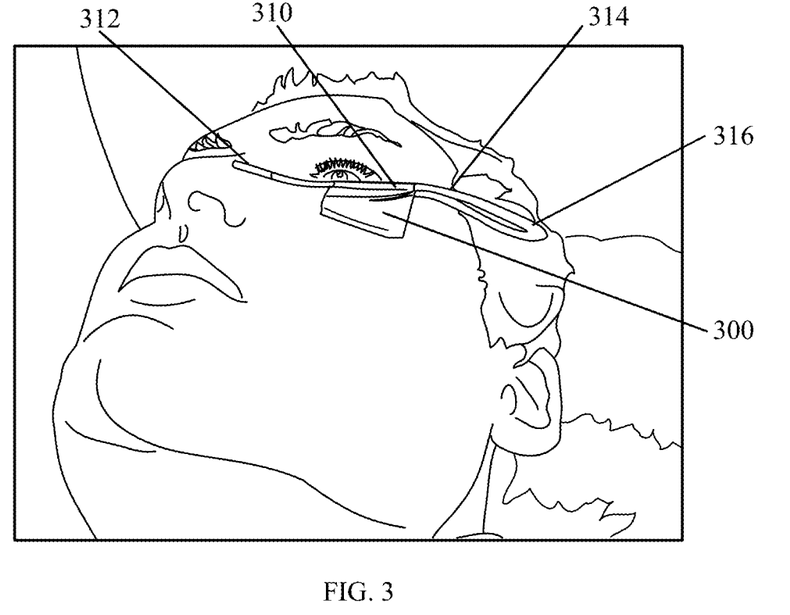
FIG. 3 shows one example of an ophthalmic infusion support in use according to an embodiment of the invention.

FIG. 3 shows an example of an ophthalmic infusion support 300, similar to infusion supports 100 and 200 discussed above. The ophthalmic infusion support 300 is shown attached to a patient adjacent to the patient's eye. An infusion tube 310 is shown coupled to the ophthalmic infusion support 300. The infusion tube 310 includes a supply end 312, and an outlet end 314. A loop 316 of the infusion tube 310 is shown adjacent to the patient's eye. The loop projects upward from the patient as a result of being coupled to the ophthalmic infusion support 300.

The loop 316, and the upward projection provide comfort to the patient by allowing the infusion tube to move slightly without any excessive forces to the patient's eye. Example infusion support devices, such as infusion supports 100, 200, 300 and other examples as described in the present disclosure, help resist the weight of the tubing that may tend to pull a tip of the infusion line into unwanted orientations. The loop 316, and the upward projection provide an infusion supply that is directed toward a desired portion of the eye, with unobstructed flow, and is much less likely to kink, twist, or otherwise become obstructed during a procedure.

Figure 4A:
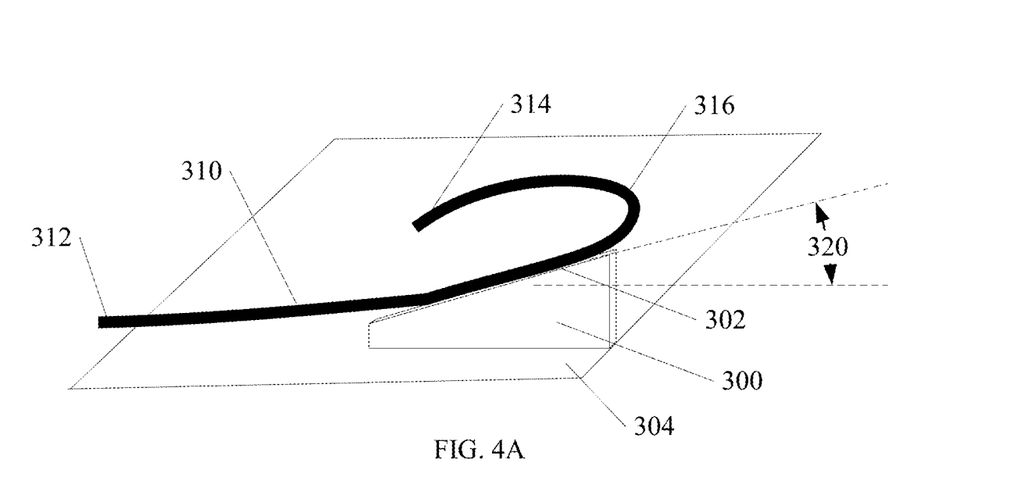
FIG. 4A shows another example of an ophthalmic infusion support according to an embodiment of the invention.
Figure 4B:
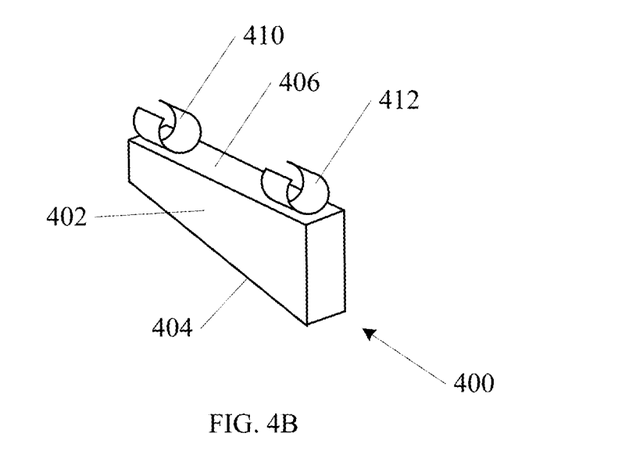
FIG. 4B shows an isometric view of an ophthalmic infusion support according to an embodiment of the invention.

FIG. 4A further illustrates how examples of ophthalmic infusion supports provide a secure loop with an upward projection. In the example of FIG. 4, the infusion tube 310 is attached to the ophthalmic infusion support 300 along a top surface. In one example, the infusion tube 310 is attached using an adhesive as described in FIGS. 1 and 2. Other examples of attachment without adhesives are described in additional examples below, including FIG. 4B. The infusion tube 310 of FIG. 4, includes a loop 316 that projects upward from the patient as depicted by surface 304. The loop 316 projects upward at an angle 320 from the surface 304. In one example, the upward projection of the loop 316 provides a downward projection of the supply end 314 of the infusion tube 310. Such a configuration provides a reliable, substantially fixed angle of supply to an eye of the patient without unwanted misdirection of infusion flow, obstruction of infusion flow, kinking, twisting, etc. of the infusion tube 310.

In the example of FIG. 4A, the upward projection of the loop 316 is a direct result of aligning the infusion tube 310 along an angled top surface of the ophthalmic infusion support 300, however, the invention is not so limited. Other configurations may use other types of infusion tube holding devices to provide an upward projection of a loop. Selected other examples are discussed in more detail below.

FIG. 4B shows an example of an ophthalmic infusion support 400, including a base unit 402 having a bottom surface 404 and a top surface 406. Similar to other example ophthalmic infusion supports (100, 200, 300) in one example the base unit 402 is substantially flat in one dimension. As described above, materials for the base unit 402 may include, but are not limited to, polymers, foamed polymers, metals, composites, etc.

In one example, the bottom surface 404 includes an adhesive coupled to the bottom surface 404. As in other examples described, the adhesive may serve as a fixation device, and may be used to attach to a patient. In one example an adhesive such as a pressure sensitive adhesive is used. A peel off backing for an adhesive may also be used in selected embodiments. As in other embodiments described, the bottom surface 404 may be flat, or curved. As discussed above, in alternate examples, other fixation devices that may be used in place of adhesive 520 include, but are not limited to, mechanical fixation, such as spring clips, pins, etc. Mechanical fixation device examples will primarily be used for indirect fixation to an intermediate element, such as a surgical drape.

In the Example of FIG. 4B, a pair of infusion tube holding devices are shown, including a first infusion tube holding device 410 and a second infusion tube holding device 412. In the example shown, the infusion tube holding devices 410, 412 include resilient clips, although the invention is not so limited. In the resilient clip example of FIG. 4B, arms of the infusion tube holding devices 410, 412 are flexible and can deform to allow insertion of an infusion tube (not shown) into the resilient clips. The pair of infusion tube holding devices 410, 412 of the ophthalmic infusion support 400 are configured to hold a portion of an infusion tube in a loop that projects upward from a patient, as shown in FIG. 4A above.

Figure 5:
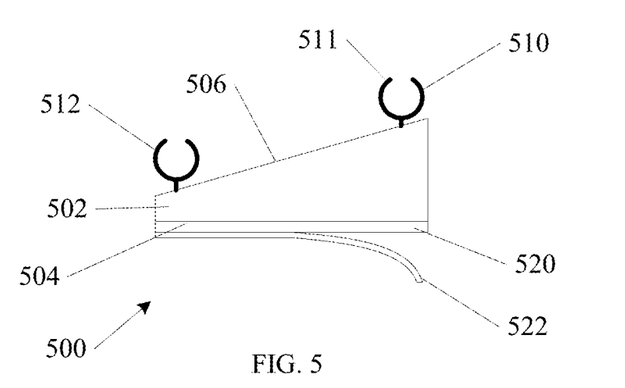
FIG. 5 shows another ophthalmic infusion support according to an embodiment of the invention.

FIG. 5 shows an example of an ophthalmic infusion support 500, including a base unit 502 having a bottom surface 504 and a top surface 506. Similar to other example ophthalmic infusion supports (100, 200, 300) in one example the base unit 502 is substantially flat in one dimension (for example in the plane of the page of FIG. 5). As described above, materials for the base unit 502 may include, but are not limited to, polymers, foamed polymers, metals, composites, etc.

The example of FIG. 5 shows a pair of infusion tube holding devices, including a first infusion tube holding device 510 and a second infusion tube holding device 512. In the example shown, the infusion tube holding devices 510, 512 include resilient clips, although the invention is not so limited. In the resilient clip example of FIG. 5, arms 511 of the infusion tube holding devices 510, 512 are flexible and can deform to allow insertion of an infusion tube (not shown) into the resilient clips. The pair of infusion tube holding devices 510, 512 of the ophthalmic infusion support 500 are configured to hold a portion of an infusion tube in a loop that projects upward from a patient, as shown in more detail in FIGS. 7 and 8 below.

Similar to other example ophthalmic infusion supports (100, 200, 300), an adhesive 520 is coupled to the bottom surface 504 of the base unit 502. The adhesive 520 serves as a fixation device, and may be used to attach to a patient, directly or indirectly as discussed above. In one example the adhesive such as a pressure sensitive adhesive is used. In the example of FIG. 5, a peel off backing 522 is shown that may be removed to expose the adhesive 520 for attaching to a patient. As discussed in other examples, the bottom surface 504 may be flat as shown in FIG. 5, or optionally anatomically curved as shown in FIG. 2 to better conform and adhere to a patient, either directly or indirectly.

As discussed above, in alternate examples, other fixation devices that may be used in place of adhesive 520 include, but are not limited to, mechanical fixation, such as spring clips, pins, etc. Mechanical fixation device examples will primarily be used for indirect fixation to an intermediate element, such as a surgical drape.

Figure 6:
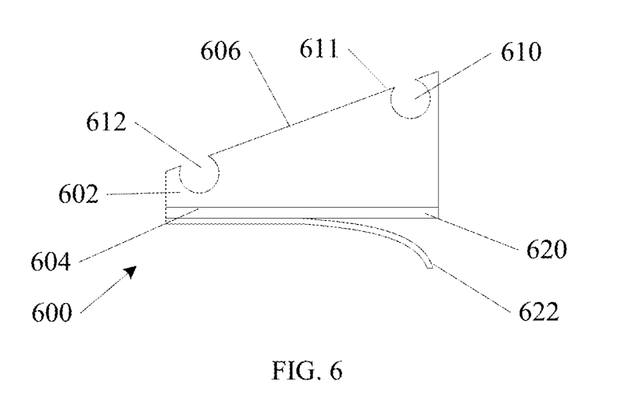
FIG. 6 shows another ophthalmic infusion support according to an embodiment of the invention.

FIG. 6 shows an example of an ophthalmic infusion support 600, including a base unit 602 having a bottom surface 604 and a top surface 606. Similar to other example ophthalmic infusion supports (100, 200, 300, 500) in one example the base unit 602 is substantially flat in one dimension although other configurations are within the scope of the invention. As described above, materials for the base unit 602 may include, but are not limited to, polymers, foamed polymers, metals, composites, etc.

The example of FIG. 6 shows a pair of infusion tube holding devices, including a first infusion tube holding device 610 and a second infusion tube holding device 612. In the example shown, the infusion tube holding devices 610, 612 include resilient clips, although the invention is not so limited.

In the resilient clip example of FIG. 6, the infusion tube holding devices 610, 612 are integrally molded or cut from the base unit 602. Similar to the example of FIG. 5, the infusion tube holding devices 610, 612 are flexible and can deform to allow insertion of an infusion tube (not shown) into the resilient clips. In one example by integrally molding or cutting the infusion tube holding devices 610, 612 from the base unit 602, manufacturing cost and materials cost savings are provided. The pair of infusion tube holding devices 610, 612 of the ophthalmic infusion support 600 are configured to hold a portion of an infusion tube in a loop that projects upward from a patient, as shown in more detail in FIGS. 7 and 8 below.

Similar to other example ophthalmic infusion supports (100, 200, 300, 500), an adhesive 620 is coupled to the bottom surface 604 of the base unit 602. The adhesive 620 serves as a fixation device, and may be used to attach to a patient, directly or indirectly as discussed above. In one example the adhesive such as a pressure sensitive adhesive is used. In the example of FIG. 6, a peel off backing 622 is shown that may be removed to expose the adhesive 620 for attaching to a patient. As discussed in other examples, the bottom surface 604 may be flat as shown in FIG. 6, or optionally anatomically curved as shown in FIG. 2 to better conform and adhere to a patient, either directly or indirectly.

As discussed above, in alternate examples, other fixation devices that may be used in place of adhesive 620 include, but are not limited to, mechanical fixation, such as spring clips, pins, etc. Mechanical fixation device examples will primarily be used for indirect fixation to an intermediate element, such as a surgical drape.

Figure 7:
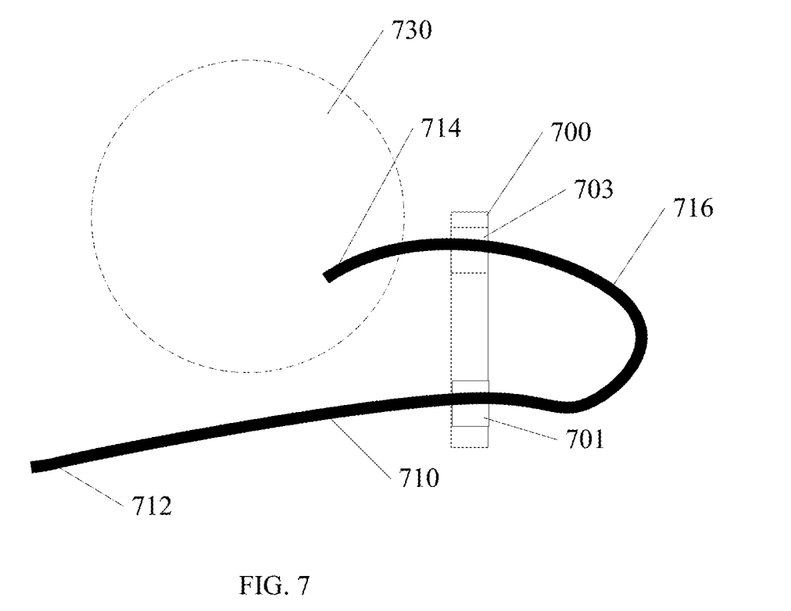
FIG. 7 shows another ophthalmic infusion support according to an embodiment of the invention.
Figure 8:
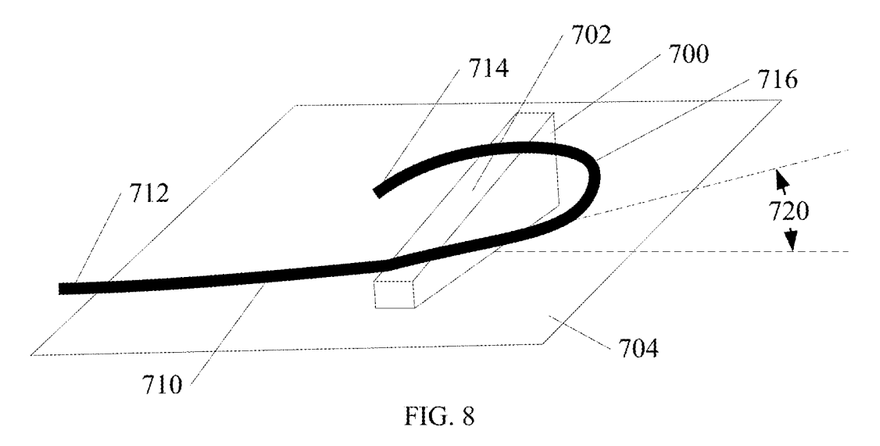
FIG. 8 shows another ophthalmic infusion support according to an embodiment of the invention.

FIGS. 7 and 8 further illustrate how examples of ophthalmic infusion supports shown in FIGS. 5 and 6 provide a secure loop with an upward projection. In the example of FIG. 7, an infusion tube 710 is attached to an ophthalmic infusion support 700. In one example, the infusion tube 710 is attached using a pair of infusion tube holding devices 701, 703, two possible examples of which are shown in FIGS. 5 and 6.

The ophthalmic infusion support 700 is shown attached to a patient adjacent to the patient's eye 730. The infusion tube 710 includes a supply end 712, and an outlet end 714. A loop 716 of the infusion tube 710 is shown adjacent to the patient's eye. The loop projects upward from the patient, as further illustrated in FIG. 8, as a result of being coupled to the ophthalmic infusion support 700.

As shown in FIG. 8, the loop 716 projects upward from the patient as depicted by surface 704. The loop 716 projects upward at an angle 720 from the surface 704. In one example, the upward projection of the loop 716 provides a downward projection of the supply end 714 of the infusion tube 710. Such a configuration provides a reliable, substantially fixed angle of supply to an eye of the patient without unwanted kinking, twisting, etc. of the infusion tube 710.

In the example of FIG. 8, the upward projection of the loop 716 is provided by the arrangement and orientation of the pair of infusion tube holding devices 701, 703. In one example, both the arrangement and orientation of the pair of infusion tube holding devices 701, 703, and the upward angle of the top surface of the base unit 702 provide the upward projection of the loop 716. The loop 716, and the upward projection provide comfort to the patient by allowing the infusion tube to move slightly without any excessive forces to the patient's eye. The loop 716, and the upward projection further provide a reliable, substantially fixed angle of supply to an eye of the patient without unwanted misdirection of infusion flow, obstruction of infusion flow, kinking, twisting, etc. of the infusion tube during a procedure.

Figure 9:
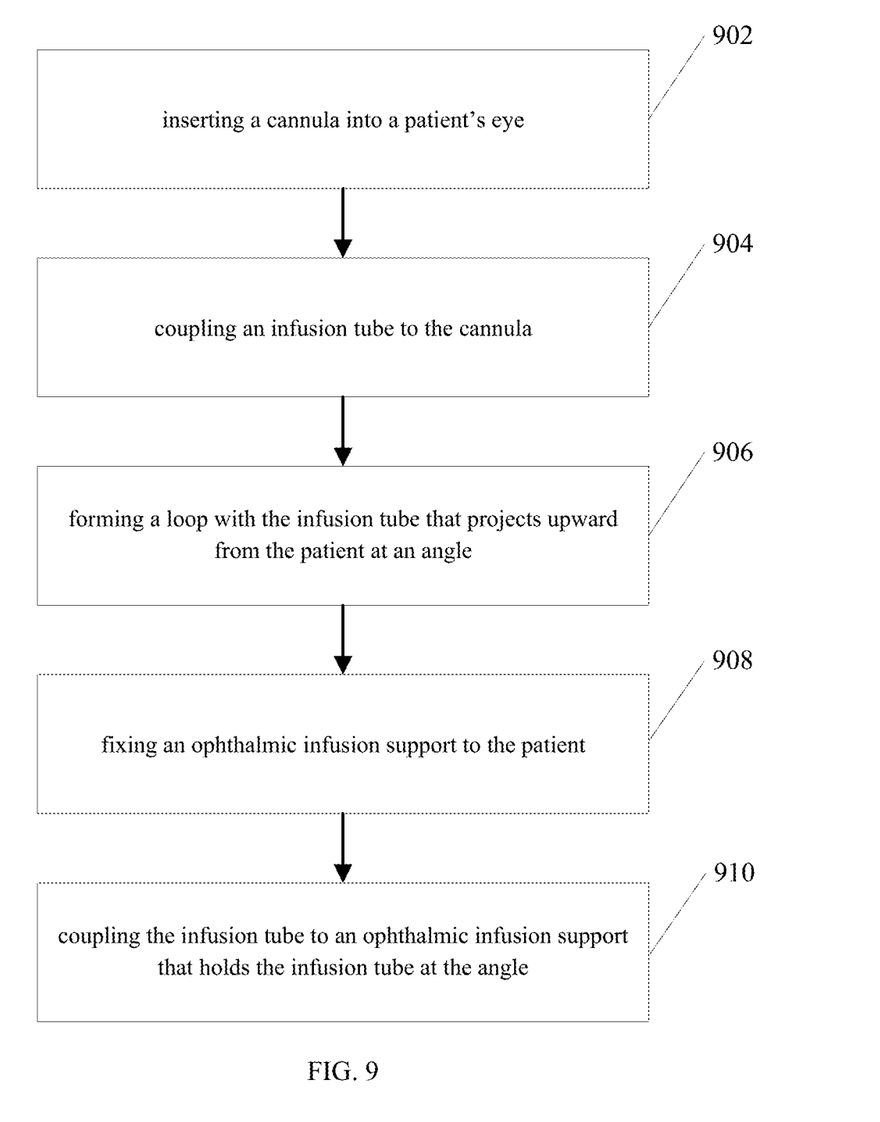
FIG. 9 shows an example method of using an ophthalmic infusion support according to an embodiment of the invention.

FIG. 9 shows a method of using an ophthalmic infusion support, such as one or more of the ophthalmic infusion supports described in examples above. In operation 902, a cannula is inserted into a patient's eye. In operation 904, an infusion tube is coupled to the cannula. In operation 906, a loop is formed with the infusion tube that projects upward from the patient at an angle. In operation 908, an ophthalmic infusion support is fixed to the patient. In operation 910, the infusion tube is coupled to an ophthalmic infusion support that holds the infusion tube at the angle.

Figure 10:
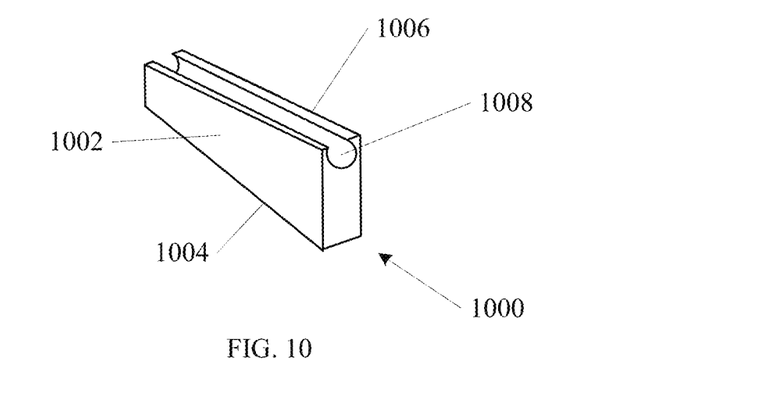
FIG. 10 shows another ophthalmic infusion support according to an embodiment of the invention.

FIG. 10 shows an example of an ophthalmic infusion support 1000, including a base unit 1002 having a bottom surface 1004 and a top surface 1006. As described above, materials for the base unit 1002 may include, but are not limited to, polymers, foamed polymers, metals, composites, etc.

In one example, the bottom surface 1004 includes an adhesive coupled to the bottom surface 1004. As in other examples described, the adhesive may serve as a fixation device, and may be used to attach to a patient. In one example an adhesive such as a pressure sensitive adhesive is used. A peel off backing for an adhesive may also be used in selected embodiments. As in other embodiments described, the bottom surface 1004 may be flat, or curved. As discussed above, in alternate examples, other fixation devices that may be used in place of adhesive include, but are not limited to, mechanical fixation, such as spring clips, pins, etc.

In the Example of FIG. 10, a single, elongated infusion tube holding device 1008 is shown. In one example, the infusion tube holding device 1008 is integrally molded or cut from the base unit 1002. Similar to the example of FIG. 5, the infusion tube holding device 1008 is flexible and can deform to allow insertion of an infusion tube (not shown). In one example by integrally molding or cutting the infusion tube holding device 1008 from the base unit 1002, manufacturing cost and materials cost savings are provided.

Figure 11:
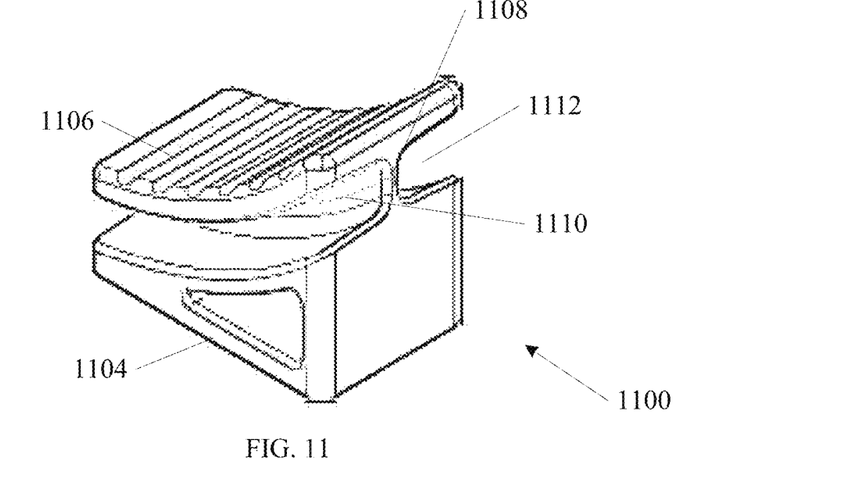
FIG. 11 shows another ophthalmic infusion support according to an embodiment of the invention.

FIG. 11 shows an example of an ophthalmic infusion support 1100, including a base unit 1102 having a bottom surface 1104. In one example, the bottom surface 1104 includes an adhesive coupled to the bottom surface 1104. As in other examples described, the adhesive may serve as a fixation device, and may be used to attach to a patient. In one example an adhesive such as a pressure sensitive adhesive is used. A peel off backing for an adhesive may also be used in selected embodiments. As in other embodiments described, the bottom surface 1104 may be flat, or curved.

As discussed above, in alternate examples, other fixation devices that may be used in place of adhesive include, but are not limited to, mechanical fixation, such as spring clips, pins, etc.

The ophthalmic infusion support 1100 example of FIG. 11 shows a first infusion tube holding device 1110 and a second infusion tube holding device 1112. In one example, the ophthalmic infusion support 1100 is wholly or partially formed from a resilient material, such as a polymer material, or flexible metal. In one resilient material example, a top portion 1106 may be tilted slightly to one side or the other in order to facilitate insertion of an infusion tube into the first or second infusion tube holding device 1110, 1112. The resilient nature of the material will then serve as a clamping force to hold the infusion tube in place within the chosen infusion tube holding device. One advantage of two infusion tube holding devices 1110, 1112 includes a greater number of options to hold the infusion tube in place without obstructing view of the eye for the procedure.

Although in one example, the entire ophthalmic infusion support 1100 is formed from a resilient material, although the invention is not so limited. In one example, only a portion, such as a connecting region 1108 is formed from a resilient material. In other examples, the ophthalmic infusion support 1100 is formed from a rigid material, and a resilient nature of the infusion tube is used to hold the tube within either one of the first or second infusion tube holding devices 1110, 1112.

In all examples shown, the infusion tube holding devices provide an important feature of permitting a user to adjust an amount of infusion tube that extends beyond an end of an ophthalmic infusion support toward the patient. This allows a user to adjust a correct length of infusion tube to provide an optimal length of tubing to form a loop that projects upward from the patient. As discussed above, in one example, the upward projection of a loop provides a downward projection of a supply end of the infusion tube. Such a configuration provides a reliable, substantially fixed angle of supply to an eye of the patient without unwanted misdirection of infusion flow, obstruction of infusion flow, kinking, twisting, etc. of the infusion tube.

To better illustrate the method and apparatuses disclosed herein, a non-limiting list of embodiments is provided here:

Example 1 includes an ophthalmic infusion support. The ophthalmic infusion support includes a base unit having a bottom surface and a top surface, a fixation device coupled to the bottom surface of the base unit to attach to a patient, and an infusion tube holding device coupled to the top surface of the base unit, wherein the infusion tube holding device is configured to hold a loop of an infusion tube an angle projecting upward from the patient.

Example 2 includes the ophthalmic infusion support of example 1, wherein the fixation device includes adhesive.

Example 3 includes the ophthalmic infusion support of any one of examples 1-2, wherein the fixation device includes a peel off backing covering the adhesive.

Example 4 includes the ophthalmic infusion support of any one of examples 1-3, wherein the infusion holding device includes adhesive.

Example 5 includes the ophthalmic infusion support of any one of examples 1-4, wherein the infusion holding device includes a peel off backing covering the adhesive.

Example 6 includes the ophthalmic infusion support of any one of examples 1-5, wherein the bottom surface is curved to match a patient's face contour.

Example 7 includes the ophthalmic infusion support of any one of examples 1-6, wherein the infusion tube holding device includes an angled top surface projecting away from the patient.

Example 8 includes the ophthalmic infusion support of any one of examples 1-7, wherein the infusion tube holding device includes a pair of infusion tube holding devices.

Example 9 includes the ophthalmic infusion support of any one of examples 1-8, wherein the infusion tube holding device includes at least one integrally formed infusion tube holding device.

Example 10 includes the ophthalmic infusion support of any one of examples 1-9, wherein the infusion tube holding device is formed from a resilient material.

Example 11 includes an ophthalmic infusion support. The ophthalmic infusion support includes a base unit having a bottom surface and a top surface, a fixation device coupled to the bottom surface of the base unit to attach to a patient, and a pair of infusion tube holding devices coupled to the top surface of the base unit, wherein the pair of infusion tube holding devices are configured to hold a portion of an infusion tube in a loop that projects upward from the patient.

Example 12 includes the ophthalmic infusion support of example 11, wherein the fixation device includes adhesive.

Example 13 includes the ophthalmic infusion support of any one of examples 11-12, wherein the fixation device includes a peel off backing covering the adhesive.

Example 14 includes the ophthalmic infusion support of any one of examples 11-13, wherein the pair of infusion tube holding devices include resilient clips.

Example 15 includes the ophthalmic infusion support of any one of examples 11-14, wherein the pair of infusion tube holding devices are integrally formed with the base unit.

Example 16 includes the ophthalmic infusion support of any one of examples 11-15, wherein the pair of infusion tube holding devices are integrally formed with the base unit.

Example 17 is a method that includes inserting a cannula into a patient's eye, coupling an infusion tube to the cannula, forming a loop with the infusion tube that projects upward from the patient at an angle, fixing an ophthalmic infusion support to the patient, and coupling the infusion tube to an ophthalmic infusion support that holds the infusion tube at the angle.

Example 18 includes the method of example 17, wherein fixing an ophthalmic infusion support to the patient includes adhering an ophthalmic infusion support to the patient.

Example 19 includes the method of any one of examples 17-18, wherein fixing an ophthalmic infusion support to the patient includes peeling an adhesive backing off to expose an adhesive, and placing the adhesive in contact with the patient.

Example 20 includes the method of any one of examples 17-19, wherein placing the adhesive in contact with the patient includes placing the adhesive directly in contact with skin of the patient.

Example 21 includes the method of any one of examples 17-20, wherein placing the adhesive in contact with the patient includes placing the adhesive in contact with a surgical drape near an eye of the patient.

Example 22 includes an ophthalmic infusion support, including a base unit, a fixation device coupled to a bottom surface of the base unit to attach to a patient, and an infusion tube holding device coupled to the base unit at an angle, wherein the infusion tube holding device is configured to hold a loop of an infusion tube an angle projecting upward from the patient.

Example 23 includes the ophthalmic infusion support of example 22, further including a second infusion tube holding device.

Example 24 includes the ophthalmic infusion support of any one of examples 22-23, wherein the ophthalmic infusion support is formed at least partially from a resilient material.

Example 25 includes the ophthalmic infusion support of any one of examples 22-24, wherein the ophthalmic infusion support is formed from a rigid material.

These and other examples and features of the present infusion devices, and related methods will be set forth in part in the above detailed description. This overview is intended to provide non-limiting examples of the present subject matter—it is not intended to provide an exclusive or exhaustive explanation.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A method, comprising:
   inserting a cannula into a patient's eye;
   coupling an infusion tube to the cannula;
   forming a loop with the infusion tube;
   fixing an ophthalmic infusion support to the patient;
   deforming a pair of resilient openings in an integrally formed portion of the ophthalmic infusion support; and
   inserting two portions of the loop into the pair of resilient openings.

2. The method of claim 1, wherein the inserting of the two portions of the loop into the pair of resilient openings includes inserting the two portions of the loop at an orientation where the loop of the infusion tube projects upward from the patient at an angle.

3. The method of claim 1, wherein the fixing of the ophthalmic infusion support to the patient includes pressing an adhesive.

4. The method of claim 3, wherein the fixing of the ophthalmic infusion support to the patient includes peeling off a backing to expose the adhesive before the pressing of the adhesive.

5. The method of claim 1, wherein the deforming of the pair of resilient openings includes deforming the integrally formed polymer portion, which includes an integrally formed polymer portion.

6. The method of claim 1, wherein the deforming of the pair of resilient openings includes deforming the integrally formed portion, which includes an integrally formed foamed polymer portion.

* * * * *